United States Patent [19]

Gooch

[11] Patent Number: 5,437,269
[45] Date of Patent: Aug. 1, 1995

[54] MOUTH TO MOUTH RESUSCITATION DEVICE WITH OPTIONAL OXYGEN AUGMENTATION

[75] Inventor: Loro W. Gooch, Pinellas Park, Fla.

[73] Assignees: Dorothy Lillian Gooch; Dale Kwilecki; Charles E. Lykes, Jr., all of Clearwater, Fla.

[21] Appl. No.: 896,224

[22] Filed: Jun. 10, 1992

[51] Int. Cl.⁶ .............................................. A61M 16/00
[52] U.S. Cl. ............................ 128/202.28; 128/203.11
[58] Field of Search ..................... 128/202.28, 202.29, 128/203.11

[56] References Cited

U.S. PATENT DOCUMENTS

| | | | |
|---|---|---|---|
| 4,449,525 | 5/1984 | White et al. | 128/203.11 |
| 4,811,730 | 3/1989 | Milano | 128/203.11 |
| 4,819,627 | 4/1989 | Connors | 128/203.11 |
| 4,819,628 | 4/1989 | Eisenberg et al. | 128/203.11 |
| 4,942,873 | 7/1990 | Irwin et al. | 128/203.11 |
| 4,998,530 | 3/1991 | DonMichael | 128/203.11 |
| 5,005,568 | 4/1991 | Loescher et al. | 128/203.11 |

Primary Examiner—Edgar S. Burr
Assistant Examiner—Aaron J. Lewis
Attorney, Agent, or Firm—Charles E. Lykes, Jr.

[57] ABSTRACT

An improved apparatus for assisting a rescuer in performing safe and effective mouth-to-mouth resuscitation on a victim. The apparatus allows a range of orientations between victim and rescuer and also allows the augmentation of the rescuer's air with oxygen, even when remote from a medical facility.

20 Claims, 4 Drawing Sheets

MOUTH TO MOUTH RESUSCITATION DEVICE WITH OPTIONAL OXYGEN AUGMENTATION

BACKGROUND OF THE INVENTION

The invention relates to first aid devices, particularly those for use in mouth-to-mouth resuscitation. Reference is made to disclosure document number 304105 filed by the inventor on Mar. 23, 1992, which is incorporated by this reference.

The development of mouth-to-mouth resuscitation as a means of reviving a victim who has ceased breathing has saved countless lives. Its original and most rudimentary form of mouth-to-mouth rescuer/victim contact presents one major danger, and has one major shortcoming. The danger is that mouth-to-mouth contact results in fluid exchange between victim and rescuer. With the advent of AIDS, Hepatitis-B, and other vaccine and antibiotic resistant diseases, this poses a serious obstacle to a potential rescuer's willingness to save an unknown victim.

The shortcoming is that, even with the enhanced ability to deliver air to a victim, the air delivered with the fundamental form of mouth-to-mouth resuscitation will normally be somewhat oxygen deficient (having been in part oxidized by the rescuer) or, at best, equal to ambient air in oxygen content. Upon interruption of the breathing function, the loss of oxygen to the brain poses a serious threat to the victim. The longer this situation continues, the more likely it becomes that the victim will suffer permanent brain damage. Accordingly, it is useful to enhance the oxygen supply available to the victim. Such an oxygen supply is normally not available at a first aid or lifeguard station nor is oxygen normally supplied in a first aid kit.

Several previous patents have posed solutions to the dangers associated with saliva exchange. For instance, U.S. Pat. No. 4,819,628, issued to Eisenberg, et al, on Apr. 11, 1989, teaches a one piece air channel with a victim mouthpiece and rescuer mouthpiece. Extending radially out from a point along its length is a planar sheet to prevent direct skin contact between victim and rescuer. Air or fluid within the channel is free to move in either direction. There is no means of augmenting the air supply with oxygen.

Several devices teach the use of one way valves within a mouth-to-mouth resuscitation apparatus in order to prevent victim air or fluid from passing to the rescuer. U.S. Pat. No. 4,942,873, issued to Irwin, et al, on Jul. 24, 1990, teaches the use of a "resiliently deformable" valving member within the first, or rescuer, piece of two pieces, which must be aligned in a "predetermined rotational orientation".

U.S. Pat. No. 5,005,568, issued to Loescher, et al, on Apr. 9, 1991, teaches a rather complex device in which victim to rescuer air flow is restricted by means of a duckbill valve. Additionally, a filter is used to purify air passing between rescuer and victim. In order to achieve the desired result, the connection means between victim and rescuer in Loescher teaches a series of annular rings in a precisely fitting orientation. Loescher also teaches the potential supplementation of the air supply by use of an elbow with adapter pipe within the channel between victim and rescuer, but teaches no means or apparatus suitable for the delivery of the oxygen. The one-way valve comprises a duckbill device which, in the absence of an air pressure differential, assumes a closed position. In order to ensure effective operation of the device with filter installed, it is necessary to maintain relative dimension relationships between the various air channel portion of the apparatus.

What is not provided by the prior art is a simple and inexpensive device which permits use in a variety of victim/rescuer orientations, restricts the flow of air to one direction, and permits, but does not require, augmentation of the air supply with oxygen at any remote location and without compromise of the operation of the device.

SUMMARY OF THE INVENTION

The present invention solves both of these problems and also improves upon the ability of the prior art devices. It additionally provides an apparatus which is inexpensive to obtain, simple to operate (even when augmenting the air supply with oxygen), and is easy to clean or sterilize.

The invention generally comprises a two piece apparatus for transmitting air from the breath of a rescuer to the lungs of a victim whose breathing has been interrupted. The apparatus prevents oral contact between victim and rescuer. It is further adapted with a swivel connection between the two to permit the rescuer to assume various positions with respect to the victim. It also has a one-way apparatus to prevent air from flowing from victim to rescuer. The victim mouthpiece may be made disposable or in various sizes.

Optionally, the apparatus may be adapted with an oxygen supply to allow the breath transmitted from the rescuer to be enhanced with additional oxygen for the benefit of the victim. Additionally, the aparatus may be adapted with a mask, or facepiece, to fit over the victim's mouth to both provide additional sanitary protection and to ensure more efficient transmission of breath from rescuer to victim.

It is, then, an object of the present invention to provide a safe and reliable means of permitting a rescuer to provide mouth-to-mouth resuscitation to a victim whose health is unknown to the rescuer.

It is a further object of the present invention to provide such an apparatus permitting the rescuer to assume a comfortable position with respect to the victim.

It is a further object of the present invention to provide such an apparatus which allows the rescuer's breath to be enhanced with additional oxygen.

It is a further object of the present invention to provide such an apparatus with a mask or facepiece in order to provide additional protection and improve the efficiency of the air exchange.

Other features and advantages of the present invention will be apparent from the following description in which the preferred embodiments have been set forth in conjunction with the accompanying drawings.

BRIEF DESCRIPTION OF THE DRAWINGS

In describing the preferred embodiments of the invention reference will be made to the series of figures and drawings briefly described below.

DETAILED DESCRIPTION

Reference will now be made In detail to the present preferred embodiment of the invention, an example of which is illustrated in the accompanying drawings. While the invention will be described in connection with a preferred embodiment, it will be understood that it is not intended to limit the invention to that embodiment. On the contrary, it is intended to cover all alternatives, modifications, and equivalents as may be included within the spirit and scope of the invention defined in the appended claims.

Figure 1:
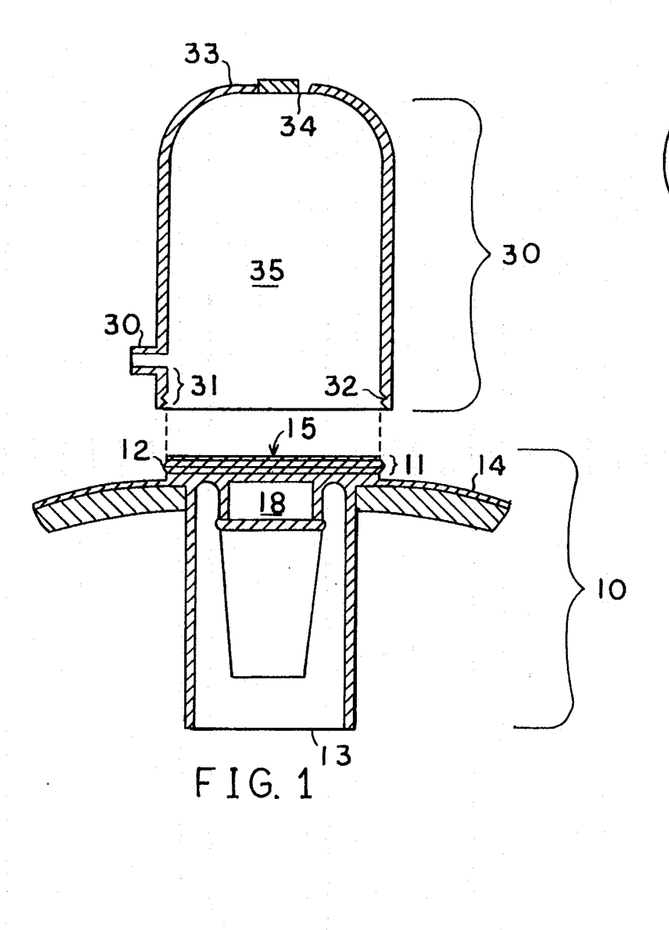
FIG. 1 depicts the victim and rescuer mouthpieces separately and indicates the means of connection.

Making reference first to FIG. 1, it can be seen that the basic components of the apparatus comprise a victim mouthpiece (generally 10) and a rescuer mouthpiece (generally 30). The victim mouthpiece (10) is adapted with a cylindrical connecting portion (11) which is adapted to slide snugly within a cylindrical receiving portion (31) of the rescuer mouthpiece (30). At or near the end of the connecting portion (11) is provided a radial protrusion (12) which goes about the exterior surface of the connecting portion (11). This radial protrusion (12) is adapted to snap into a radial slot (32) around the inner surface of the receiving portion (31).

In this manner, the victim mouthpiece (10) and rescuer mouthpiece (30) can fit together. Furthermore, the victim mouthpiece (10) can be rotated within the rescuer mouthpiece (30) since the connection facilitated by the snapping of the radial protrusion (12) into the radial slot (32) does not prohibit the rotation of either mouthpiece (10,30) with respect to the other. Within the connecting portion (11) is a connecting channel (15), permitting air to flow through the connecting portion (11).

The victim mouthpiece (10) has a bottom end (13) which is of a size to permit its insertion into a victim's mouth. It also may (but need not) be adapted with a mask or facepiece (14) which is made of a flexible material of sufficient rigidity so that it can conform to, and then maintain, a sealing position about a victim's mouth.

The rescuer mouthpiece (30) has a top end (33) which is adapted with a hole (34) to permit a rescuer to blow air into the interior portion (35) of the rescuer mouthpiece (30). The rescuer mouthpiece (30) may also (but need not) be adapted with a receiving port (36) which permits the flow of oxygen or another fluid or gas from a hose (37) into the interior portion (35).

Figure 2A:
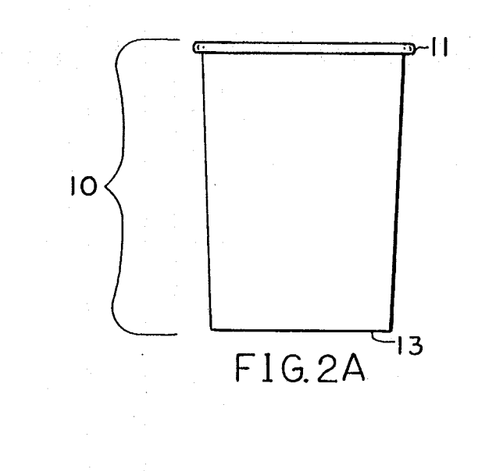
FIGS. 2A, 2B and 2C depict the front, side, and bottom views of the victim mouthpiece without a mask, respectively.
Figure 2B:
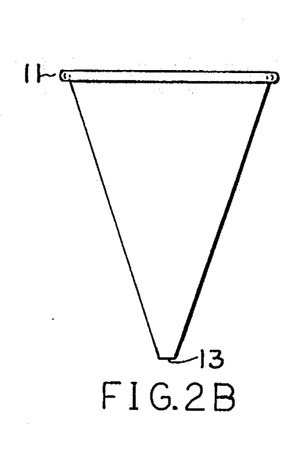
Figure 2C:
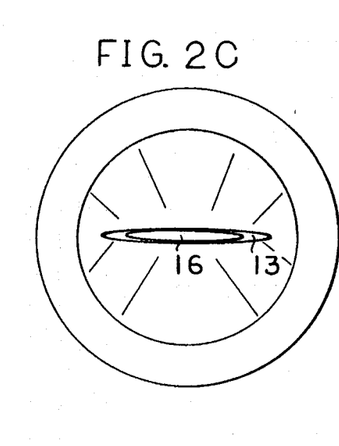

Making reference to FIGS. 2A, 2B, and 2C, the exterior portions of the victim mouthpiece are depicted. From the front view (FIG. 2A) it can be seen that the length of the victim mouthpiece (10) is only slightly tapered from the connecting portion (11) to the bottom end (13). From the side view (FIG. 2B), however, it can be seen that this tapering is more pronounced. From the bottom view (FIG. 2C) it can be seen that the bottom end (13) is generally ovular, with an opening (16) through which air can pass.

It should be pointed out that the tapering depicted in FIG. 2A can be made more or less pronounced from the connecting portion (11) to the bottom end (13) in order to permit efficient fitting into larger or smaller mouths. Accordingly, various sizes of victim mouthpieces (10) could be made with a connecting portion (11) of a standard size to permit interchangeability of victim mouthpieces (10).

Figure 3:
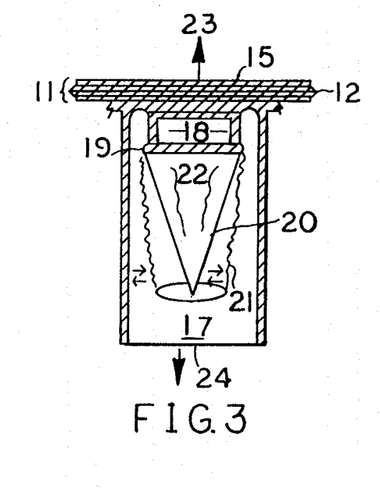
FIG. 3 depicts the interior of the victim mouthpiece in which the air passage is adapted with a one-way flow restrictor.

Considering now the interior of the victim mouthpiece, reference will be made to FIG. 3. It can be seen that the connecting channel (15) permits the flow of air into the tapered interior (17) of the victim mouthpiece (10) through a channel extension (18). About the channel extension (18) may be placed the holding end (19) of a one-way bladder skin (20), which is free to assume an open position (21) or a closed position (22). When the air pressure on the rescuer side (23) of the channel extension (18) is higher, the bladder skin (20) assumes the open bladder position (21) and air is free to flow towards the opening (16). If air pressure becomes higher on the victim side (24), however, the bladder skin (20) assumes the closed bladder position (22) and air flow is stopped.

The bladder selected for use in the preferred embodiment resembles a burst balloon. The thin skin has no real equilibrium position, but will react as described above. Very little air pressure is required to operate it. It should be pointed out that such a bladder apparatus is only one of several ways in which the flow of air can be restricted to only one way. Such other flow restriction means should be considered within the spirit and scope of the present invention.

It can now be seen that the victim mouthpiece (10) permits the virtual free flow of air from the rescuer mouthpiece (30) through its tapered interior (17) and out through its opening (16). It can also be seen that it is possible to make victim mouthpieces (10) of various size openings (16) which can all connect to a standard rescuer mouthpieces (30).

Figure 4:
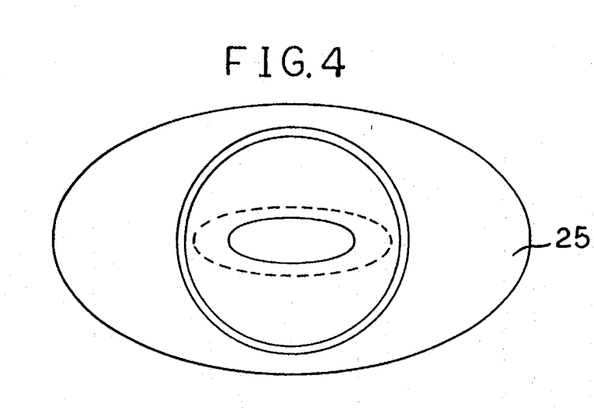
FIG. 4 depects a top view of a victim mouthpiece adapted with a mask or facepiece.
Figure 7A:
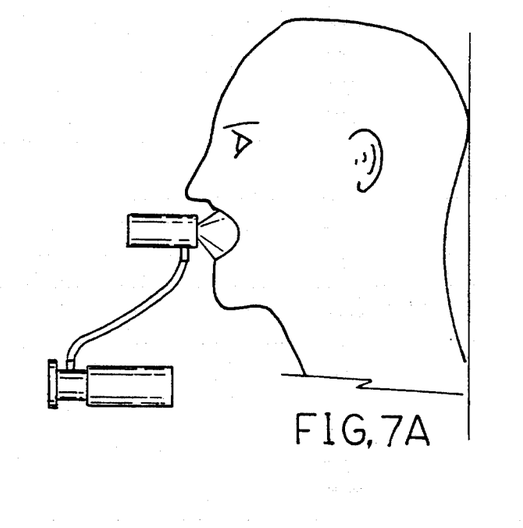
FIGS. 7A and 7B depict the apparatus in a victim's mouth with and without a mask, respectively.
Figure 7B:
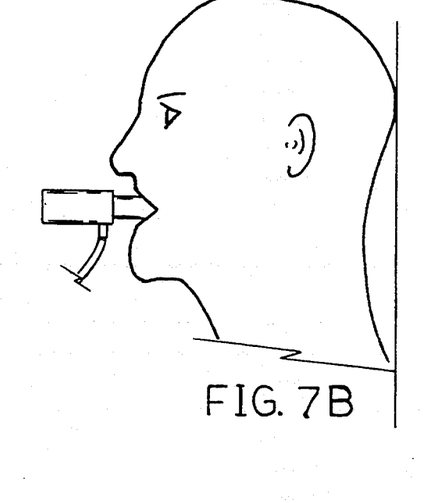

Making reference now to FIG. 4, it can be seen that the victim mouthpiece (10) can be further adapted with a mask member (25). The mask member (25) may be made of a material which is flexible enough to conform to the contour of a victim's face (FIG. 7B) but rigid enough to make a seal contact about the victim's mouth.

Figure 5:
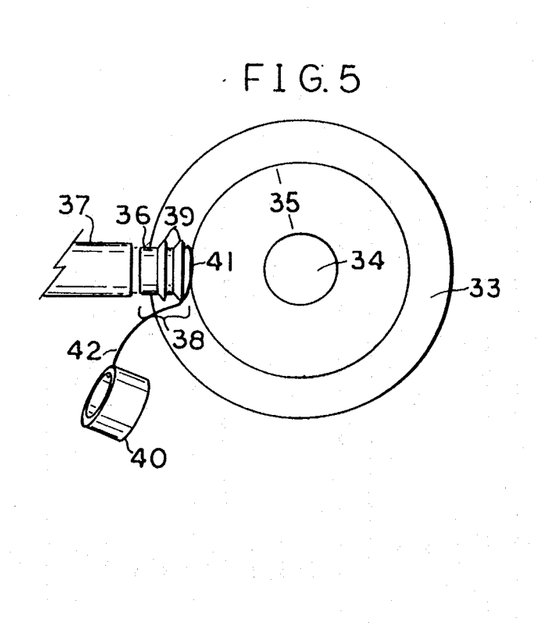
FIG. 5 depicts a top view of the rescuer mouthpiece which further depicts a port for receiving a flow of oxygen.

Making reference to FIG. 5, it can be seen that the rescuer's mouthpiece (30) comprises a top end (33) which is adapted with a hole (34). The top end (33) should be of a dimension suitable for fitting within the mouth of a person able to perform mouth-to-mouth resuscitation. The hole (34) should be of satisfactory size to permit a flow of air adequate to supply a non-breathing victim. It should be noted that an assumption is made here that small children are not likely to be rescuers using mouth-to-mouth resuscitation. Accordingly, it would not be as disirable to have a variety of sizes of rescuer mouthpieces as with victim mouthpieces since a single size would typically be acceptable for both older children and adults.

It should also be noted that, while a cylindrical tip end (33) is depicted, the rescuer mouthpiece could also be tapered from its mouth-receiving top end (33), as long as the receiving portion (31) had a cylindrical interior surface as has been described.

Also depicted in FIG. 5 is a receiving port (36). The receiving port (36) is a rigid, substantially cylindrical channel of adequate length (38) to receive a hose (37, FIG. 1, not depicted in FIG. 5). This length (38) may, but need not, be further adapted with radial wedges (39) around its surface to permit a hose (not depicted in FIG.

5) to easily slide over the length (38), but not back off of the length (38).

Additionally, a cap (40) may, but need not, be connected to the length by a ring (41) and connecting length (42). The cap (40) could then be placed over to seal the receiving port (36) when oxygen is either not available or desired or removed when oxygen is used. The connecting ring (41) and connecting length (42) ensure that the cap (40) will not be lost when removed. It should be noted that, even if the cap (40) is lost and oxygen is not available, the apparatus could be effectively used by placing a finger over the receiving port (36) to prevent the escape of air from the rescuer mouthpiece (30).

Figures 6, 6A:
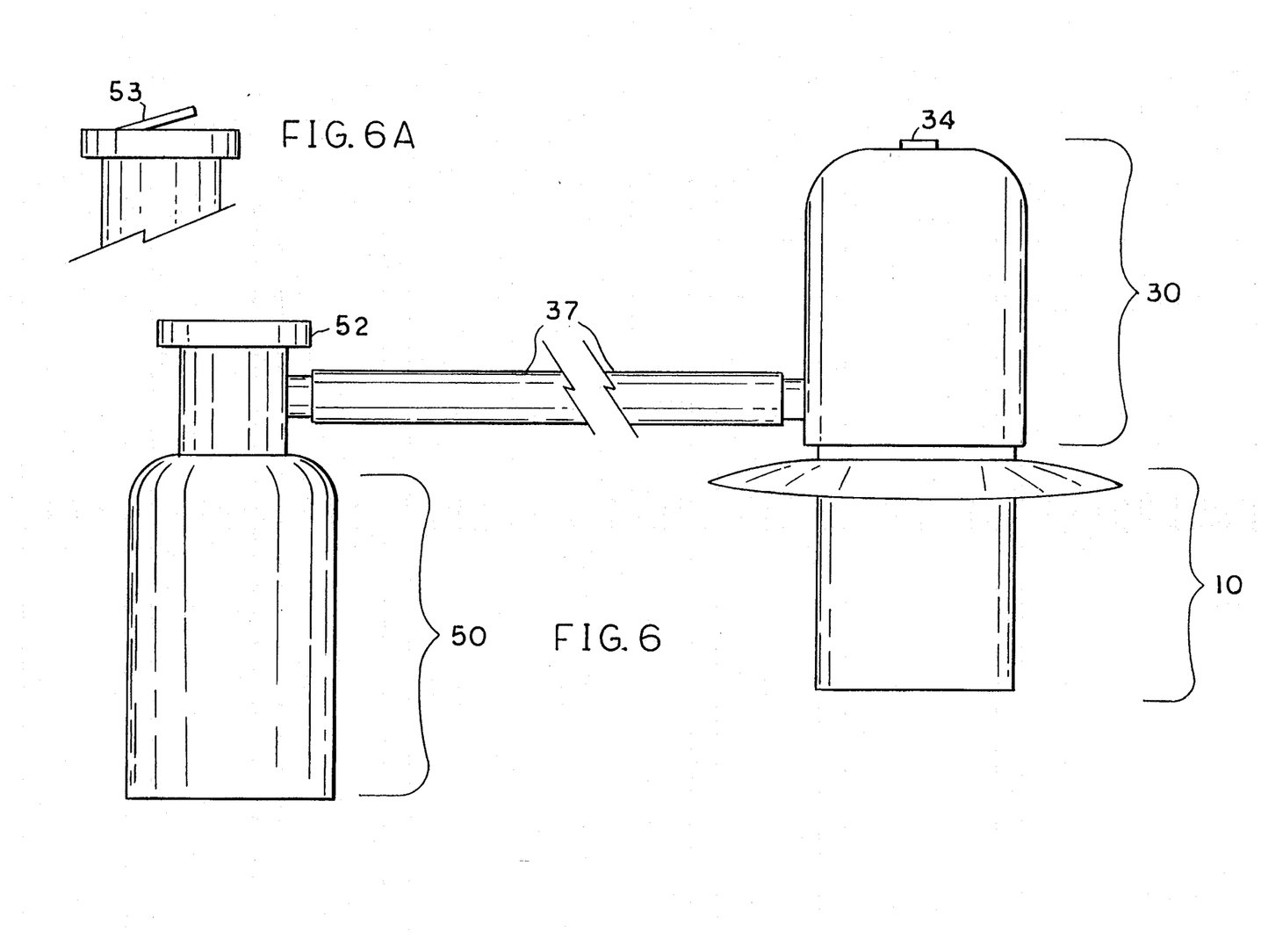
FIG. 6 depicts the overall apparatus connected to a supply of oxygen with ring control.
FIG. 6A represents a push button oxygen control.

Making reference now to FIG. 6, it can be seen that an oxygen supply (50) can be provided to supply oxygen through the hose (37) and receiving port (38) in to the interior portion (35) of the rescuer mouthpiece (30). The oxygen therein mixes with the rescuer breath from the hole (34) and the pressure from the rescuer breath forces the mixture into the victim mouthpiece (10).

It is envisioned that the oxygen supply could be one such as the model 5002 by Leland. This is a personal sized pressurized oxygen tank which holds about 18 liters of oxygen at atmospheric pressure in a hand-held tank (51), or about a 20 minute supply. With such a supply, a valving ring (52) could be set at a desired level and left alone during a rescuing operation. If, however, it was necessary to operate with a smaller oxygen supply or to control the oxygen supply more closely, a push button valve (53) could be used.

Certain specific variations or alternative means to the preferred embodiment should be mentioned. Larger, less mobile, supplies of oxygen could also be used. While the invention has been described with respect to the augmentation of the air with oxygen, it should also be considered that other gases or vapors of benefit to a victim could be included. The one-way membrane type valve could also be replaced by any reasonably sized and effective one-way valve, such as (but not limited to) those described in the prior art patents. Other connection means could be used. For instance, the slot and protrusion could be on the rescuer external and victim internal surfaces (preserving the rotational function), or another connection means could be used altogether not preserving the rotational function. It is also pointd out that the invention has been developed with simple and inexpensive components. To further enhance the safety aspects of the invention, it should be noted that the mouthpieces, particularly the victim mouthpiece, could be disposable. Such variations would be in keeping with the spirit and scope of the invention.

Further modification and variation can be made to the disclosed embodiments without departing from the subject and spirit of the invention as defined in the following claims. Such modifications and variations, as included within the scope of these claims, are meant to be considered part of the invention as described.

What is claimed is:

1. A first aid apparatus useful in facilitating safe mouth-to-mouth resuscitation, the apparatus comprising:
   a rescuer mouthpiece, which comprises a rescuer mouth port of dimension permitting rescuer person's mouth to make airtight connection and blow into said rescuer mouthpiece, a fluid or gas chamber, a rescuer fluid or gas outlet, said rescuer fluid or gas outlet further comprising a cylindrical rescuer connection means for a connection with a victim mouthpiece, and
   a victim mouthpiece which comprises a cylindrical victim connection means adapted to make a snug connection with said cylindrical rescuer connection means but permit rotation of said victim mouthpiece with respect to said rescuer mouthpiece, a fluid or gas inlet port in fluid or gaseous communication with said rescuer fluid or gas outlet at said rescuer end which is adapted with flow restriction apparatus at a victim chamber end so as to permit fluid or gas to flow from said rescuer end to said to said victim chamber, but not from said victim chamber to said rescuer end, and a generally oblong victim outlet port in fluid or gaseous communication with said victim chamber, said victim mouthpiece further tapered from said rescuer mouthpiece connection means to said victim outlet port, said victim outlet port being of a size to easily fit within a victim person's mouth and said tapered portion being of adequate length to thrust into a victim person's mouth and over a victim person's tongue.

2. The first aid apparatus described in claim 1 in which said rescuer connection means comprises a slot around the circular interior surface of said rescuer fluid outlet and said circular victim connection means comprises a short cylindrical portion about said fluid inlet port which is adapted with a small protrusion about its exterior surface, said exterior surface further adapted to closely fit within said cylindrical interior surface of said rescuer fluid outlet and said small protrusion adapted to alternatively snap in or out of said slot, the connection further adapted to permit free fluid or gas flow between said rescuer chamber and said victim inlet port, to prevent the flow of fluid or gas through said slot and to permit stable but releasable connection between said rescuer mouthpiece and said victim mouthpiece and to further permit rotation of said victim mouthpiece with respect to said rescuer mouthpiece.

3. The first aid apparatus described in claim 2 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end.

4. The first aid apparatus described in claim 2 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

5. The first aid apparatus described in claim 3 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

6. The first aid apparatus described in claim 1 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end.

7. The first aid apparatus described in claim 6 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

8. The first aid apparatus described in claim 1 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

9. The first aid apparatus described in claim 1 in which said victim mouthpiece is further adapted with a mask member, said mask member being attached radially outward from said connection means of said victim mouthpiece and being generally concave so as to open toward said victim outlet port and being constructed of a nonporous material of such structural rigidity such that, under slight and steady pressure, said mask member will conform to the contours of a victim's face and seal the victim's mouth from air or fluid from outside of the apparatus.

10. The first aid apparatus described in claim 9 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end; and an oxygen supply, said oxygen supply comprising a tank of compressed oxygen, said tank of dimensions such that it can be easily held in a person's hand and stored in a small container which also houses said rescuer mouthpiece and one or more said victim mouthpieces, said tank being further adapted with a valve to control the rate of flow of said oxygen from said tank into a hose, said hose being adapted to snugly fit over said port protruding from said rescuer mouthpiece.

11. A first aid apparatus useful in facilitating safe mouth-to-mouth resuscitation, the apparatus comprising:

a rescuer mouthpiece, which comprises a rescuer mouth port of dimension permitting a rescuer person's mouth to make airtight connection and blow into said rescuer mouthpiece, a fluid or gas chamber, a rescuer fluid or gas outlet, said rescuer fluid or gas outlet further comprising a cylindrical rescuer connection means for a connection with a victim mouthpiece;

a victim mouthpiece which comprises a cylindrical victim connection means adapted to make a snug connection with said cylindrical rescuer connection means but permit rotation of said victim mouthpiece with respect to said rescuer mouthpiece, a fluid or gas inlet port in fluid or gaseous communication with said rescuer fluid or gas outlet at said rescuer end which is adapted with flow restriction apparatus at a victim chamber end so as to permit fluid or gas to flow from said rescuer end to said victim chamber, but not from said victim chamber to said rescuer end, and a victim outlet port in fluid or gaseous communication with said victim chamber, said victim mouthpiece further tapered from said rescuer mouthpiece connection means to a generally oblong victim outlet port, said victim outlet port being of a size to easily fit within a victim person's mouth and said tapered portion being of adequate length to thrust into a victim person's mouth and over a victim person's tongue;

said rescuer mouthpiece being further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end; and an oxygen supply, said oxygen supply comprising a tank of compressed oxygen, said tank of dimensions such that it can be easily held in a person's hand and stored in a small container which also houses said rescuer mouthpiece and one or more said victim mouthpieces, said tank being further adapted with a valve to control the rate of flow of said oxygen from said tank into a hose, said hose being adapted to snugly fit over said port protruding from said rescuer mouthpiece.

12. The first aid apparatus described in claim 11 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

13. The first aid apparatus described in claim 11 in which said victim mouthpiece is further adapted with a mask member, said mask member being attached radially outward from said connection means of said victim mouthpiece and being generally concave so as to open toward said victim outlet port and being constructed of a nonporous material of such structural rigidity such that, under slight and steady pressure, said mask member will conform to the contours of a victim's face and seal the victim's mouth from air or fluid from outside of the apparatus.

14. The first aid apparatus described in claim 13 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end; and an oxygen supply, said oxygen supply comprising a tank of compressed oxygen, said tank of dimensions such that it can be easily held in a person's hand and stored in a small container which also houses said rescuer mouthpiece and one or more said victim mouthpieces, said tank being further adapted with a valve to control the rate of flow of said oxygen from said tank into a hose, said hose being adapted to snugly fit over said port protruding from said rescuer mouthpiece.

15. The first aid apparatus described in claim 11 in which said rescuer connection means comprises a slot around the circular interior surface of said rescuer fluid outlet and said circular victim connection means comprises a short cylindrical portion about said fluid inlet port which is adapted with a small protrusion about its exterior surface, said exterior surface further adapted to closely fit within said cylindrical interior surface of said rescuer fluid outlet and said small protrusion adapted to alternatively snap in or out of said slot, the connection further adapted to permit free fluid or gas flow between said rescuer chamber and said victim inlet port, to prevent the flow of fluid or gas through said slot and to permit stable but releasable connection between said rescuer mouthpiece and said victim mouthpiece and to further permit rotation of said victim mouthpiece with respect to said rescuer mouthpiece.

16. The first aid apparatus described in claim 15 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end; and an oxygen supply, said oxygen supply comprising a tank of compressed oxygen, said tank of dimensions such that it can be easily held in a person's hand and stored in a small container which also houses said rescuer mouthpiece and one or more said victim mouthpieces, said tank being further adapted with a valve to control the rate of flow of said oxygen from said tank into a hose, said hose being adapted to snugly fit over said port protruding from said rescuer mouthpiece.

17. A first aid apparatus useful in facilitating safe mouth-to-mouth resuscitation, the apparatus comprising:

a rescuer mouthpiece, which comprises a rescuer mouth port of dimension permitting a rescuer person's mouth to make airtight connection and blow into said rescuer mouthpiece, a fluid or gas chamber, a rescuer fluid or gas outlet, said rescuer fluid or gas outlet further comprising a cylindrical rescuer connection means for a connection with a victim mouthpiece;

a victim mouthpiece which comprises a cylindrical victim connection means adapted to make a snug connection with said cylindrical rescuer connection means but permit rotation of said victim mouthpiece with respect to said rescuer mouthpiece, a fluid or gas inlet port in fluid or gaseous communication with said rescuer fluid or gas outlet at said rescuer end which is adapted with flow restriction apparatus at a victim chamber end so as to permit fluid or gas to flow from said rescuer end to said victim chamber, but not from said victim chamber to said rescuer end, and a generally oblong victim outlet port in fluid or gaseous communication with said victim chamber, said victim mouthpiece further tapered from said rescuer mouthpiece connection means to said victim outlet port, said victim outlet port being of a size to easily fit within a victim person's mouth and said tapered portion being of adequate length to thrust into a victim person's mouth and over a victim person's tongue;

said victim mouthpiece being further adapted with a mask member, said mask member being attached radially outward from said connection means of said victim mouthpiece and being generally concave so as to open toward said victim outlet port and being constructed of a nonporous material of such structural rigidity such that, under slight and steady pressure, said mask member will conform to the contours of a victim's face and seal the victim's mouth from air or fluid from outside of the apparatus.

18. The first aid apparatus described in claim 17 in which said flow restriction apparatus comprises a thin and flexible non-porous generally cylindrical sheet which has a means of attachment at said victim chamber end and in which said sheet is constructed of such a material such that a pressure causing the flow of gas or fluid from said victim chamber end will open said sheet cylinder to permit the flow of gas but that a pressure causing the the flow of fluid or gas toward said victim chamber end will cause said sheet to constrict and collapse and block the flow of fluid or gas into said victim chamber end.

19. The first aid apparatus described in claim 17 in which said rescuer connection means comprises a slot around the circular interior surface of said rescuer fluid outlet and said circular victim connection means comprises a short cylindrical portion about said fluid inlet port which is adapted with a small protrusion about its exterior surface, said exterior surface further adapted to closely fit within said cylindrical interior surface of said rescuer fluid outlet and said small protrusion adapted to alternatively snap in or out of said slot, the connection further adapted to permit free fluid or gas flow between said rescuer chamber and said victim inlet port, to prevent the flow of fluid or gas through said slot and to permit stable but releasable connection between said rescuer mouthpiece and said victim mouthpiece and to further permit rotation of said victim mouthpiece with respect to said rescuer mouthpiece.

20. The first aid apparatus described in claim 19 in which said rescuer mouthpiece is further adapted with a port, said port adapted to accept the flow of a fluid or gas, such as oxygen, into said rescuer chamber or be closed to prevent such flow, said port further comprising a generally cylindrical protrusion from the exterior surface of said rescuer mouthpiece which is open on its external end and adapted to snugly receive either the end of a flexible hose to permit fluid communication between said flexible hose and said rescuer chamber or to snugly receive a cap, said cap being adapted to prevent the flow of fluid through said protrusion and in which said cap may, but need not, be permanently attached to said rescuer mouthpiece with a flexible line such that said cap will always be accessible to said exterior port end; and an oxygen supply, said oxygen supply comprising a tank of compressed oxygen, said tank of dimensions such that it can be easily held in a person's hand and stored in a small container which also houses said rescuer mouthpiece and one or more said victim mouthpieces, said tank being further adapted with a valve to control the rate of flow of said oxygen from said tank into a hose, said hose being adapted to snugly fit over said port protruding from said rescuer mouthpiece.

* * * * *